United States Patent
Umino et al.

(10) Patent No.: US 10,488,337 B1
(45) Date of Patent: Nov. 26, 2019

(54) LASER GAS ANALYZER

(71) Applicant: YOKOGAWA ELECTRIC CORPORATION, Tokyo (JP)

(72) Inventors: Yusaku Umino, Musashino (JP); Junichi Matsuo, Musashino (JP)

(73) Assignee: YOKOGAWA ELECTRIC CORPORATION, Tokyo (JP)

( * ) Notice: Subject to any disclaimer, the term of this patent is extended or adjusted under 35 U.S.C. 154(b) by 0 days.

(21) Appl. No.: 16/406,793

(22) Filed: May 8, 2019

(30) Foreign Application Priority Data

May 11, 2018 (JP) .................................. 2018-092398

(51) Int. Cl.
*G01N 21/00* (2006.01)
*G01N 21/61* (2006.01)

(52) U.S. Cl.
CPC .................................... *G01N 21/61* (2013.01)

(58) Field of Classification Search
CPC ............. G01N 21/1702; G01N 21/171; G01N 21/1717; G01N 21/255; G01N 29/2418
USPC ........................................................ 356/432
See application file for complete search history.

(56) References Cited

U.S. PATENT DOCUMENTS

| | | | |
|---|---|---|---|
| 2006/0215163 A1* | 9/2006 | Friedrichs | G01N 21/15 356/439 |
| 2012/0033218 A1 | 2/2012 | Hokamura et al. | |
| 2013/0161544 A1 | 6/2013 | Ohnishi et al. | |
| 2017/0248517 A1* | 8/2017 | Scherer | G01N 21/61 |

FOREIGN PATENT DOCUMENTS

JP        5813409 B2       11/2015

* cited by examiner

*Primary Examiner* — Md M Rahman
(74) *Attorney, Agent, or Firm* — Osha Liang LLP (57) ABSTRACT

A laser gas analyzer includes: an optical emitter that irradiates laser light onto a measurement target gas; a reflector that reflects the laser light after the laser light passes through the measurement target gas; an optical receiver that receives the reflected laser light; a controller that controls the optical emitter and processes an output signal from the optical receiver; a tubular measurement target gas passage disposed between the optical emitter and the reflector and that includes an opening that allows the measurement target gas to flow into and out of the measurement target gas passage; a first purge region disposed on the optical emitter side of the measurement target gas passage; and a first separation wall that separates the measurement target gas passage and the first purge region and that includes a hole through which the laser light passes.

4 Claims, 6 Drawing Sheets

LASER GAS ANALYZER

CROSS-REFERENCE TO RELATED APPLICATION

The present application claims priority from Japanese Patent Application No. 2018-92398 filed May 11, 2018, the entire contents of which are incorporated herein by reference in its entirety.

TECHNICAL FIELD

The present invention relates to a laser gas analyzer.

BACKGROUND

A known type of analyzer for detecting the concentration of various gases, such as CO, $CO_2$, and $O_2$, is a laser gas analyzer. The laser gas analyzer irradiates laser light onto a gas to be measured and takes advantage of how the laser light is absorbed by the gas present in the optical path of the laser light.

Patent literature (PTL) 1, for example, discloses a probe for gas analysis as such a laser gas analyzer. The probe includes a purge air supplier, a sample gas inlet, and a second sample gas inlet in a tubular member.

PATENT LITERATURE

PTL 1: JP5813409B2

SUMMARY

A laser gas analyzer according to one or more embodiments the present invention includes:

an optical emitter configured to irradiate laser light onto a measurement target gas;

a reflector configured to reflect the laser light after the laser light passes through the measurement target gas;

an optical receiver configured to receive the laser light reflected by the reflector;

a controller configured to control the optical emitter and process an output signal from the optical receiver;

a tubular measurement target gas passage disposed between the optical emitter and the reflector and comprising an opening such that the measurement target gas flows into and out of the measurement target gas passage via the opening;

a first purge region disposed on the optical emitter side of the measurement target gas passage and filled with a purge gas not including a component to be measured; and a first separation wall defining a boundary between the measurement target gas passage and the first purge region and comprising a hole through which the laser light can pass;

wherein a surface of the first separation wall facing the optical emitter has a minute unevenness formed thereon to promote diffusion of the laser light or has been subjected to surface treatment to promote diffusion or absorption of the laser light.

DETAILED DESCRIPTION

In the gas analysis probe disclosed in PTL 1, no physical boundary is provided for suppressing the movement of the purge gas towards the center of the measurement location. Accordingly, the optical path length of laser light exposed to the sample gas cannot be stabilized, leaving room for improvement in the measurement accuracy of component concentration.

One or more embodiments of the present invention provide a laser gas analyzer with improved measurement accuracy of component concentration.

A laser gas analyzer according to one or more embodiments of the present invention includes:

an optical emitter configured to irradiate laser light onto a measurement target gas;

a reflector configured to reflect the laser light after the laser light passes through the measurement target gas;

an optical receiver configured to receive the laser light reflected by the reflector;

a controller configured to control the optical emitter and process an output signal from the optical receiver;

a tubular measurement target gas passage disposed between the optical emitter and the reflector and comprising an opening such that the measurement target gas flows into and out of the measurement target gas passage via the opening;

a first purge region disposed on the optical emitter side of the measurement target gas passage and filled with a purge gas not including a component to be measured; and a first separation wall defining a boundary between the measurement target gas passage and the first purge region and comprising a hole through which the laser light can pass;

wherein a surface of the first separation wall facing the optical emitter has a minute unevenness formed thereon to promote diffusion of the laser light or has been subjected to surface treatment to promote diffusion or absorption of the laser light. This configuration achieves an effect not attainable with PTL 1, namely the provision of a physical boundary between the measurement target gas passage and the purge region to stabilize the optical path length of exposure to the measurement target gas while suppressing unwanted light returning to the optical receiver due to provision of the physical boundary, thereby improving the accuracy with which the component concentration of the measurement target gas is detected.

The laser gas analyzer according to one or more embodiments further includes a second purge region disposed on the reflector side of the measurement target gas passage and filled with a purge gas and a second separation wall defining a boundary between the measurement target gas passage and the second purge region and comprising a hole through which the laser light can pass. A surface of the second separation wall facing the optical emitter may have a minute unevenness formed thereon to promote diffusion of the laser light or has been subjected to surface treatment to promote diffusion or absorption of the laser light. This configuration can provide a physical boundary between the measurement target gas passage and the purge region to further stabilize the optical path length of exposure to the measurement target gas and can cause only laser light that has traversed the intended optical path to return to the optical receiver.

The surface treatment in the laser gas analyzer according to one or more embodiments is blasting. This configuration allows the surface treatment required for removal of unwanted light to be performed easily and inexpensively.

In the laser gas analyzer of one or more embodiments, the position of the optical emitter may be adjustable relative to the first separation wall in direction orthogonal to the optical axis. This configuration allows the laser light to be adjusted so as to pass through the center of the hole provided in the separation wall, making the laser light less likely to be blocked by the wall portion of the separation wall if the probe vibrates. Furthermore, the position of the optical emitter can be readjusted if the laser light is blocked due to the probe bending under its own weight.

One or more embodiments of the present invention provide a laser gas analyzer with improved measurement accuracy of component concentration.

Figure 1:
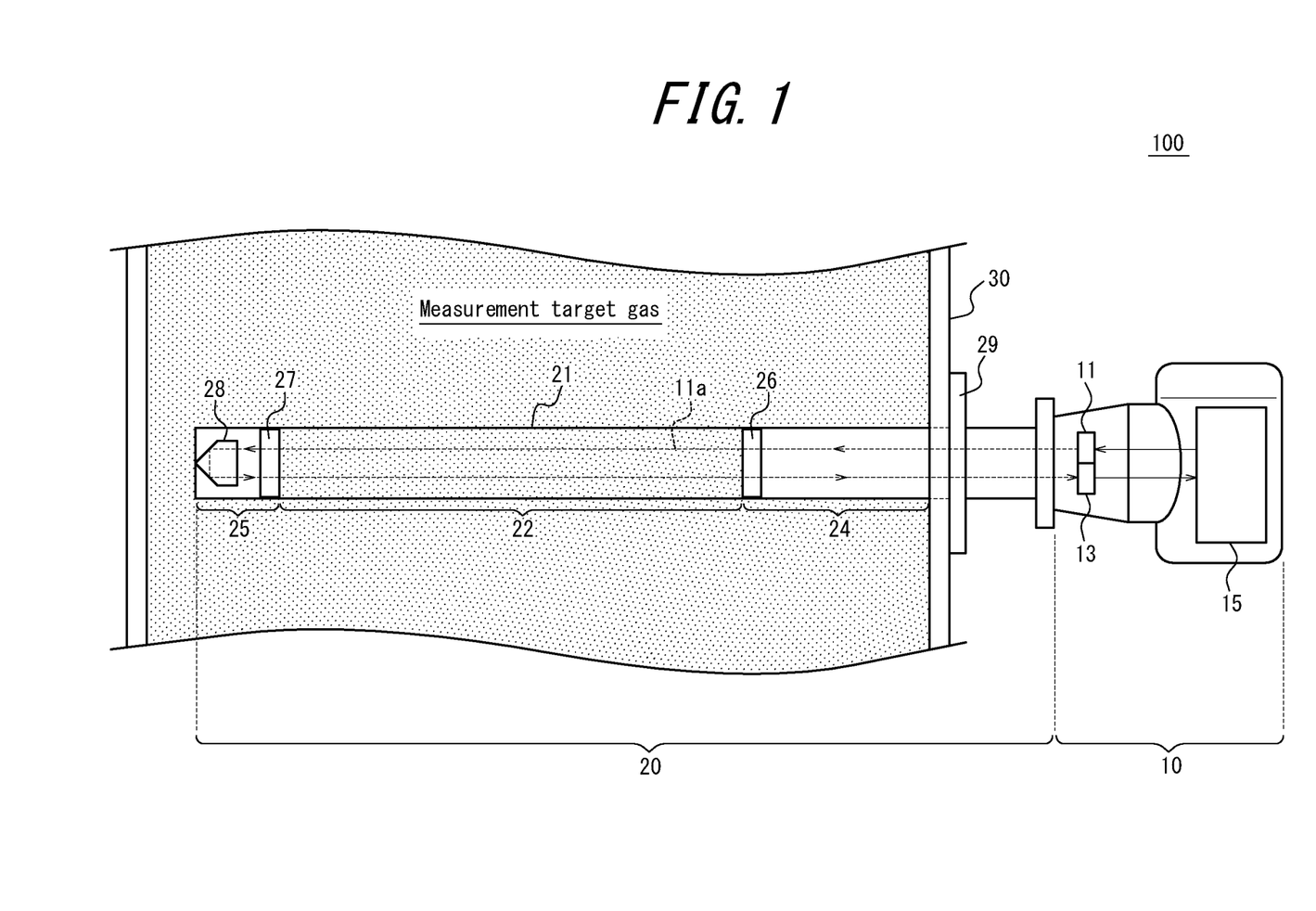
FIG. 1 is a conceptual diagram of a laser gas analyzer according to one or more embodiments of the present invention.

Embodiments of the present invention are now described with reference to the drawings. As illustrated in FIG. 1, a laser gas analyzer 100 according to one or more embodiments includes a probe 20 and an analysis unit 10. The probe 20 has a measurement target gas passage 22 of a predetermined optical path length defined therein and subjects laser light 11a to light absorption by exposure to a measurement target gas over a predetermined optical path. The analysis unit 10 irradiates the laser light 11a onto the measurement target gas, receives the laser light 11a subjected to light absorption in the probe 20, and analyzes the measurement target gas. The measurement target gas referred to here is a gas including components to be measured such as CO, $CO_2$, and/or $O_2$ and may include one or a plurality of components to be measured.

In the present description, claims, abstract, and drawings, the optical axis direction is a direction along the emission direction of the laser light 11a. This is the left-right direction in FIG. 1. An optical emitter 11 side is the right side in FIG. 1, and a reflector 28 side is the left side in FIG. 1.

As illustrated in FIG. 1, the analysis unit 10 includes an optical emitter 11 that emits the laser light 11a and irradiates the laser light 11a onto the measurement target gas, an optical receiver 13 that receives the laser light 11a subjected to light absorption by the measurement target gas, and a controller 15 that controls the optical emitter 11 and processes the output signal from the optical receiver 13.

The optical emitter 11 includes a laser that emits the laser light 11a and a laser drive circuit that supplies current to the laser. A wavelength-tunable semiconductor laser capable of sweeping (scanning) a wavelength in a range that includes the absorption wavelength of the measurement target gas can, for example, be used as the laser. The laser drive circuit can include a transistor, a laser drive integrated circuit (IC), or the like capable of supplying drive current to the laser on the basis of a control signal from the controller 15. As indicated by the arrow in FIG. 1, the laser light 11a emitted by the optical emitter 11 is irradiated in a substantially orthogonal direction (the left direction in FIG. 1) to the direction in which the measurement target gas flows (downward in FIG. 1).

The optical receiver 13 receives the laser light 11a that was irradiated from the optical emitter 11 and subjected to light absorption by being exposed to the measurement target gas in the measurement target gas passage 22. The optical receiver 13 may, for example, include a light-receiving element such as a photodiode, a voltage conversion circuit that converts the photodetection current from the light-receiving element to voltage, and an amplifier. The optical receiver 13 detects the optical intensity of incident laser light 11a using the light-receiving element and outputs the optical intensity to the controller 15 and the like. The light-receiving element may be an element other than a photodiode.

The controller 15 controls the optical emitter 11 and also processes the output signal from the optical receiver 13. Control of the optical emitter 11 includes control of the emission wavelength of the laser light 11a, the emission power of the laser light 11a, and the pulse width and duty ratio of the emission pulse. Processing of the output signal from the optical receiver 13 includes processing such as i) calculation of the absorption spectrum of the received laser light 11a on the basis of the output signal and ii) calculation of the components included in the measurement target gas, and the concentration of the components, on the basis of the absorption spectrum.

Figure 2:
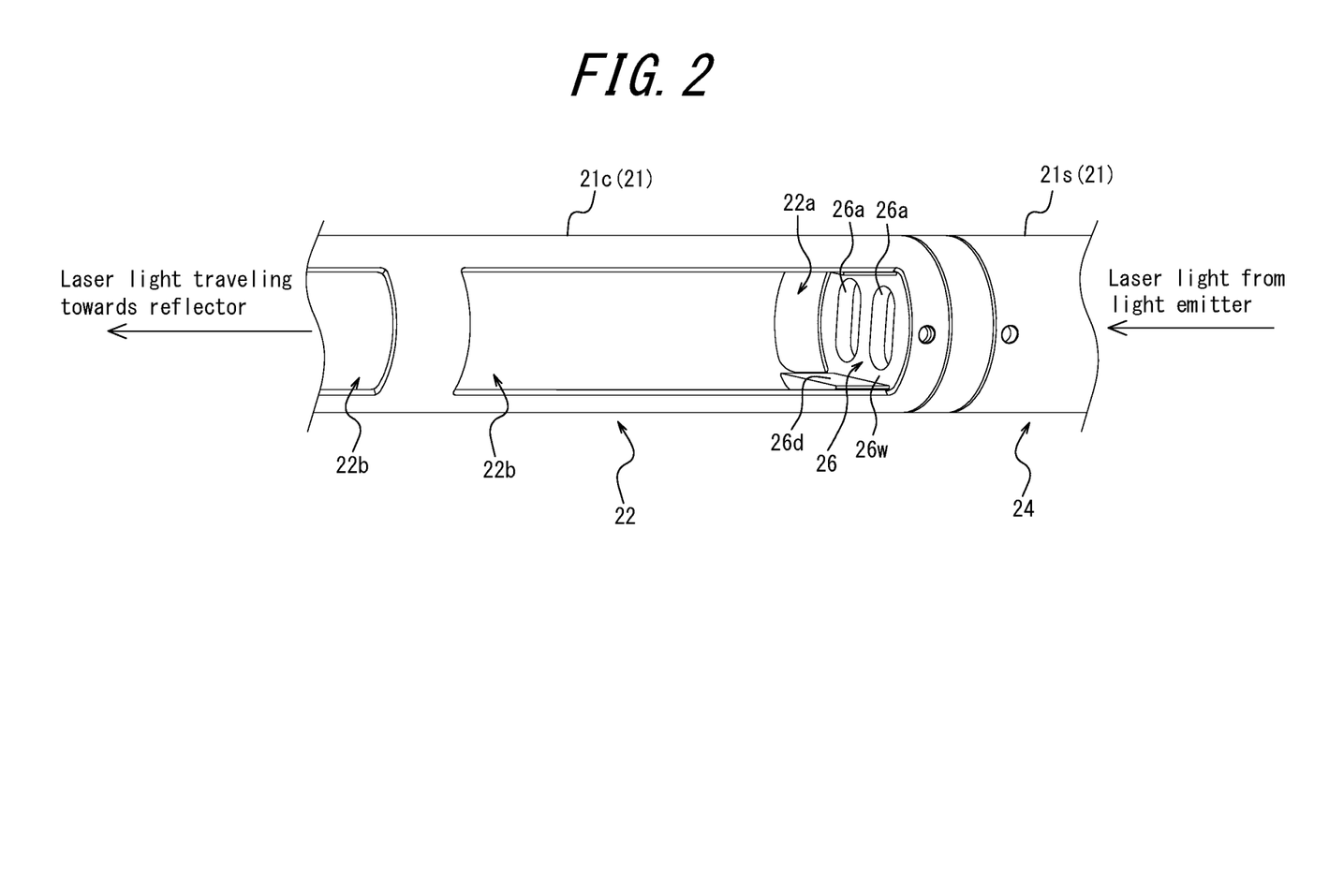
FIG. 2 is an enlarged perspective view near a separation wall on an optical emitter side in the laser gas analyzer according to one or more embodiments of the present invention.

Next, the configuration of the probe 20 is described. As illustrated in FIG. 1, the probe 20 is arranged inside a pipe 30, through which the measurement target gas flows, so that the longitudinal direction of the probe 20 is orthogonal to the flow of the measurement target gas. The probe 20 includes the measurement target gas passage 22 that defines the optical path length of the laser light 11a exposed to the measurement target gas and purge regions 24, 25 (first purge region, second purge region) arranged on either side of the measurement target gas passage 22 in the optical axis direction and filled with a purge gas. The probe 20 is arranged so that the measurement target gas passage 22 is away from the wall of the pipe 30 and is in an area with a relatively large velocity distribution of the flowing measurement target gas. The measurement target gas passage 22 and the purge regions 24, 25 are compartmentalized by a tubular housing 21 that forms the outer shape of the probe 20. As illustrated in FIG. 2, the housing 21 includes a central housing 21c forming the outer shape of the measurement target gas passage 22 and side housings 21s forming the outer shape of the purge regions 24, 25. In one or more embodiments, the position of the optical emitter 11 is adjustable, in direction orthogonal to the optical axis, relative to separation walls 26, 27 (first separation wall, second separation wall), described below. The laser light 11a can thereby be adjusted to pass through an optimal position within holes 26a, 27a provided in the separation walls 26, 27.

The separation walls 26, 27 are provided on either side of the measurement target gas passage 22 in the optical axis direction. Boundaries between the measurement target gas passage 22 and the purge regions 24, 25 are formed by the separation walls 26, 27. FIG. 2 is an enlarged perspective view near the separation wall 26 on the optical emitter 11 side.

The separation wall 26 (first separation wall) includes a wall portion 26w and two holes 26a formed in the wall portion 26w, as illustrated in FIG. 2. The wall portion 26w defines the boundary between the measurement target gas passage 22 and the purge region 24 (first purge region) on the optical emitter 11 side. In one or more embodiments, the two holes 26a are formed to be an appropriate size at positions allowing the laser light 11a emitted from the optical emitter 11 and the laser light 11a reflected by the reflector 28 respectively to pass through, as illustrated in FIG. 1. Larger holes 26a can be formed to reduce the probability of the laser light 11a being blocked by the portion surrounding the holes 26a, so that the laser light 11a stably strikes the optical receiver 13 even when the probe 20 vibrates due to a disturbance, or when the probe 20 deforms by bending for reasons such as its own weight. The purge gas is supplied to the purge regions 24, 25 from a non-illustrated purge gas supplier and is discharged out of the purge regions 24, 25 through the holes 26a. Accordingly, excessively large holes 26a result in a large amount of purge gas discharged through the holes 26a, reducing economic efficiency. Furthermore, excessively large holes 26a cause the boundary between the measurement target gas passage 22 and the purge regions 24, 25 to become vague, which increases the likelihood of errors in the length of the optical path exposed to the measurement target gas. This length, however, is the basis for component concentration calculation in laser gas analysis. Accordingly, the size of the holes 26a may be determined by taking into consideration the balance between resistance to disturbances such as vibration, economic efficiency, and the required detection accuracy of component concentration.

In one or more embodiments, two holes 26a are provided in the separation wall 26, but this example is not limiting. The number of holes 26a may vary in accordance with the number of optical emitters 11 and optical receivers 13, the optical path design, and the like. It suffices to provide a hole 26a at least at one location, and holes 26a may be provided at three or more locations.

The purge gas supplied to the purge regions 24, 25 from the non-illustrated purge gas supplier may be a gas in which the components to be measured of the measurement target gas are not included. $N_2$, for example, may be used as the purge gas.

In FIG. 2, the background is the upstream side of the measurement target gas, and the foreground is the downstream side of the measurement target gas. Accordingly, the measurement target gas flows from the background to the foreground in a substantially vertical direction on the page in FIG. 2. References to the upstream side and downstream side in the explanation below respectively refer to the upstream side of the measurement target gas and the downstream side of the measurement target gas. As illustrated, the measurement target gas passage 22 includes an upstream opening 22a and downstream openings 22b.

As illustrated in FIG. 2, an upstream opening 22a is provided on the upstream side of the central housing 21c, adjacent to the separation wall 26 on the reflector 28 side (the left in FIG. 2) in the optical axis direction. The upstream opening 22a has a rectangular shape with shorter sides in the optical axis direction than in the up-down direction of FIG. 2. The measurement target gas flowing into the measurement target gas passage 22 through the upstream opening 22a passes by the holes 26a of the separation wall 26 and flows downstream. The purge gas flowing out of the holes 26a of the separation wall 26 can be prevented from flowing in the direction towards the central position of the measurement target gas passage 22 in the optical axis direction (to the left in FIG. 2) by the flow of the measurement target gas passing through the upstream opening 22a. By the upstream opening 22a that is narrow in the optical axis direction being arranged on the upstream side in this way, dust or the like that is larger than the upstream opening 22a can be prevented from entering the measurement target gas passage 22. An upstream opening 22a is also provided adjacent to the separation wall 27 on the reflector 28 side, as described below.

As illustrated in FIG. 2, a plurality of downstream openings 22b are provided along the optical axis direction on the downstream side of the central housing 21c. The downstream openings 22b are rectangular, with longer sides in the optical axis direction. The downstream side of the central housing 21c thus has large-area openings. By the downstream openings 22b that are wide in the optical axis direction being arranged on the downstream side, the measurement target gas flowing into the measurement target gas passage 22 through the upstream openings 22a can be discharged through the downstream openings 22b, and the measurement target gas wrapping around the outside of the central housing 21c to reach the downstream side can also easily be drawn inside. Dust or the like wrapping around the outside of the central housing 21c to reach the downstream side continues downstream due to its own inertial force. Hence, the amount of dust or the like entering the measurement target gas passage 22 through the downstream openings 22b is reduced.

Figure 3A:
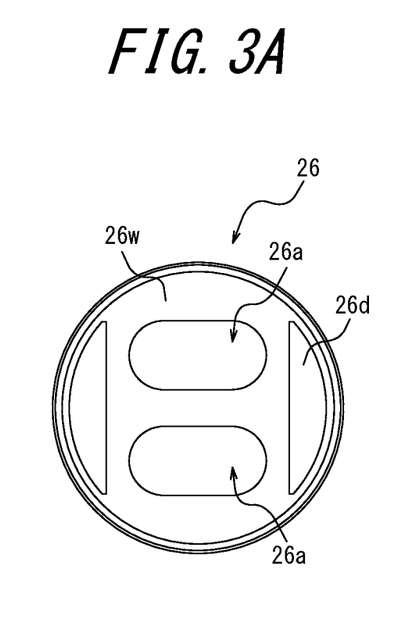
FIG. 3A illustrates the configuration of the separation wall on the optical emitter side.
Figure 3B:
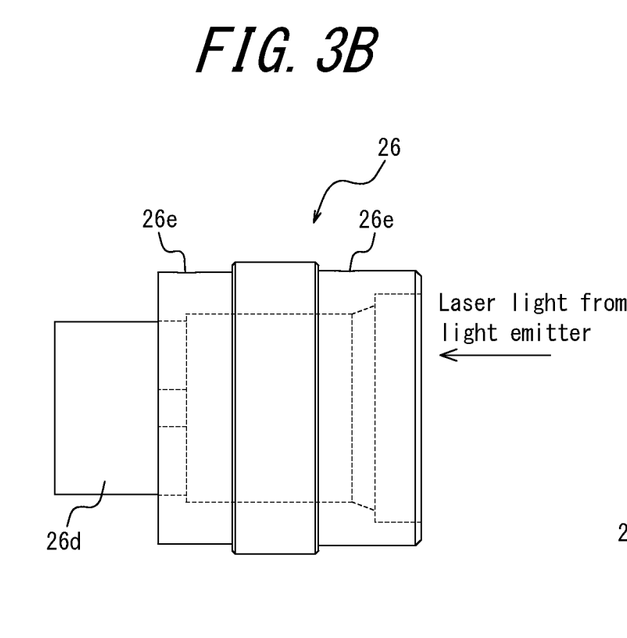
FIG. 3B illustrates the configuration of the separation wall on the optical emitter side.
Figure 3C:
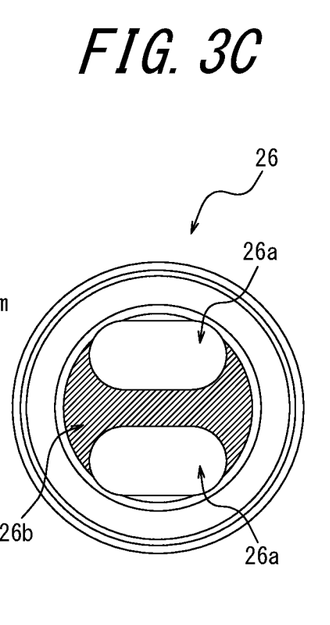
FIG. 3C illustrates the configuration of the separation wall on the optical emitter side.

FIG. 3A through FIG. 3C illustrate the separation wall 26 in FIG. 2, where FIG. 3A is a left view, FIG. 3B is a front view, and FIG. 3C is a right view. The separation wall 26 includes a wall portion 26w that defines the boundary between the measurement target gas passage 22 and the purge region 24, two holes 26a formed in the wall portion 26w, a mating portion 26e for mating and fixing the separation wall 26 to both the central housing 21c and the side housing 21s, and a guide 26d for guiding the mating portion 26e into the central housing 21c when the separation wall 26 is mated and fixed to the central housing 21c. The separation wall 26 can be made of material such as SUS316. This example is not limiting, however. The separation wall 26 can be made of various other metal materials.

FIG. 3C is a right view of the separation wall 26, illustrating the separation wall 26 as seen from the direction of incidence of the laser light 11a. The hatched portion in FIG. 3C indicates a blasted surface 26b that has been subjected to blast treatment (blasting). In one or more embodiments, the separation wall 26 is produced by cutting SUS316, and each cut face has a nearly mirror-like surface roughness. Blasting the surface that faces the optical emitter 11, however, can improve measurement accuracy by suppressing the amount of reflected light that is unwanted for laser gas analysis but returns to the optical receiver 13. In greater detail, a mechanical disturbance may vibrate the cantilevered probe 20 illustrated in FIG. 1, causing a portion of the laser light 11a to strike the blasted surface 26b without passing through the holes 26a. In this case, the laser light 11a reflected by the blasted surface 26b is diffused, which can reduce the amount of light returning to the optical receiver 13.

The blasted surface 26b is blasted with an abrasive having a large particle size, thereby finishing the blasted surface 26b to a high surface roughness. The diffuse reflection component of light reflected by the blasted surface 26b can therefore be increased, effectively reducing the amount of light returning to the optical receiver 13.

The measurement target gas may be a high temperature gas. SUS316, which is a metal material that can withstand high temperatures, is therefore used as the material of the separation walls 26, 27 in one or more embodiments, but this example is not limiting. Various metal materials other than SUS316, and alloys thereof, can be used as the material of the separation walls 26, 27. Materials other than metal materials may also be used. The separation walls 26, 27 may be manufactured by a method other than the above-described cutting, such as lost wax casting.

The purge region 24 is disposed on the optical emitter 11 side of the measurement target gas passage 22, as illustrated in FIG. 1 and FIG. 2. The purge region 24 is a region partitioned by the side housing 21s and the separation wall 26 and filled by purge gas supplied from the non-illustrated purge gas supplier. The supplied purge gas is discharged through the holes 26a of the separation wall 26. The purge gas does not include the components to be measured. The internal optical parts and the like can be protected from dust and other matter by the purge region 24 being filled with the purge gas. Furthermore, thus filling the purge region 24 with the purge gas can prevent the measurement target gas from flowing into the purge region 24, thereby maintaining a stable optical path length over which the laser light 11a is exposed to the measurement target gas.

Here, the principle of the laser gas analyzer 100 is explained, along with the reason why the measurement accuracy is increased by decreasing the amount of reflected light at the separation wall 26.

Figure 4:
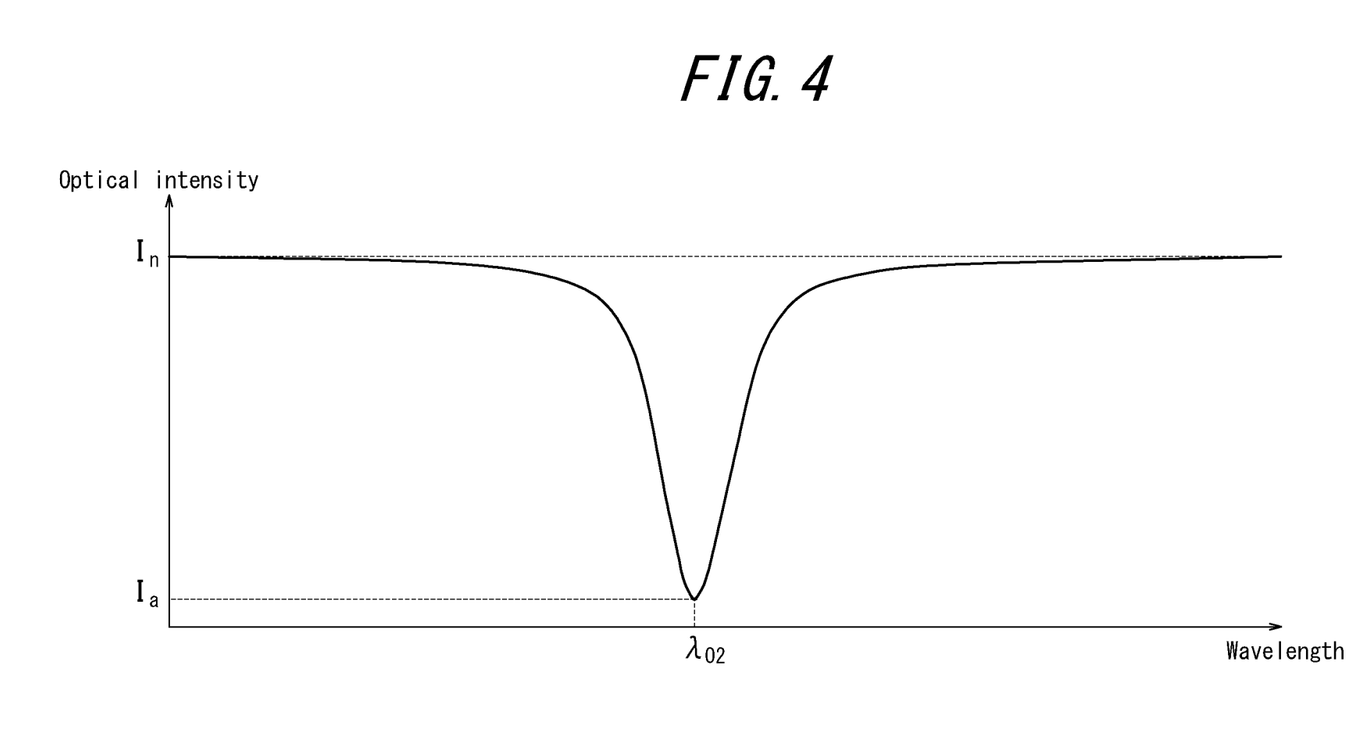
FIG. 4 illustrates an example of the absorption spectrum when the component to be measured is $O_2$.

The laser gas analyzer 100 of one or more embodiments is based on Tunable Diode Laser Absorption Spectroscopy (TDLAS). In TDLAS, semiconductor laser light with a line width far narrower than the gas absorption line width is irradiated onto the measurement target gas, and the drive current is modulated at high speed to sweep (scan) the wavelength. The amount of transmitted light is measured to measure one independent absorption spectrum. In greater detail, the laser light 11a emitted from the optical emitter 11 is exposed to the measurement target gas in the measurement target gas passage 22, which has a predetermined optical path length, as illustrated in FIG. 1. The optical emitter 11 changes the wavelength of the emitted laser light 11a over a predetermined range by continuously changing the magnitude of the drive current that drives the laser. The wavelengths absorbed by the measurement target gas depend on the measurement target gas. FIG. 4 illustrates the optical spectrum of the laser light 11a, detected by the optical receiver 13 after being emitted from the optical emitter 11 and traversing the measurement target gas passage 22 back and forth, when the component to be measured is $O_2$. As illustrated, $O_2$ has a spectrum with an absorption line at the wavelength $\lambda_{O2}$. The optical intensity decreases locally at the wavelength $\lambda_{O2}$ as compared to the optical intensity of other nearby wavelengths. The optical emitter 11 sweeps the wavelength of the laser light 11a over a predetermined wavelength range that includes the wavelength $\lambda_{O2}$ where the optical intensity decreases locally. The range over which the wavelength is swept is determined to obtain a flat curve, where the optical intensity is independent of wavelength, on the shorter and longer wavelength sides of the wavelength $\lambda_{O2}$, as illustrated in FIG. 4. The scan range of the laser light 11a differs depending on the application. For example, when the component to be measured is $O_2$, the line width of the laser light 11a is 0.0002 nm, for example, and the scan range is 0.1 to 0.2 nm, for example. The absorption spectrum is measured by scanning this range of 0.1 to 0.2 nm.

In one or more embodiments, the wavelength of the laser light 11a is swept by changing the drive current supplied to the laser. Accordingly, the optical receiver 13 actually detects different optical intensities at the wavelength by the left edge and at the wavelength by the right edge of FIG. 4. The controller 15 flattens the baseline so that the optical intensity of the wavelength by the left edge and the optical intensity of the wavelength by the right edge of FIG. 4 become equal.

The absorption Ab can be represented by Equation (1) below, where the optical intensity before incidence on the measurement target gas is $I_n$, and the optical intensity after incidence on the measurement target gas is $I_a$.

$$Ab = -\log_{10}\left(\frac{I_a}{I_n}\right) \quad (1)$$

By the Lambert-Beer law, the absorbance Ab of the measurement target gas is proportional to the component concentration of the measurement target gas and the optical path length of the laser light 11a exposed to the measurement target gas. Accordingly, the component concentration of the measurement target gas can be detected by i) identifying the optical intensity $I_n$ before incidence on the measurement target gas and the optical intensity $I_a$ after incidence on the measurement target gas from the optical spectrum illustrated in FIG. 4 to calculate the absorbance Ab, and then ii) determining the optical path length of the laser light 11a exposed to the measurement target gas. In the example illustrated in FIG. 1, the optical path length of the laser light 11a exposed to the measurement target gas is two times the length a, in the optical axis direction, of the measurement target gas passage 22. The reason is that the laser light 11a emitted from the optical emitter 11 is reflected by the reflector 28 substantially 180° towards the direction of incidence of the laser light 11a and returns to the optical receiver 13, thereby being exposed to the measurement target gas over an optical path of length 2a.

In one or more embodiments, the spectral area method is used as a method of concentration conversion, but this example is not limiting. The peak height method, the 2f method, and the like may also be used.

During detection of the component concentration of the measurement target gas with the aforementioned method, it is assumed that the optical receiver 13 only detects the laser light 11a that was emitted from the optical emitter 11 and reflected by the reflector 28. As described above, however, the laser light 11a may be blocked by the wall portion 26w and return to the optical receiver 13 if the probe 20 vibrates and causes the relative positions of the laser light 11a and the separation walls 26, 27 to change. The component concentration of the measurement target gas detected in this case is now examined.

The component concentration calculated by the laser gas analyzer 100 (concentration index x of the laser gas analyzer 100) can be represented by Equation (2) below, where in Table 1, A is the actual component concentration of the measurement target gas in the measurement target gas passage 22, B is the actual component concentration of the measurement target gas in the purge regions 24, 25, C is the transmittance of the laser light 11a passing through the measurement target gas passage 22 and returning to the optical receiver 13, and D is the transmittance of the laser light 11a reflected in the purge region 24 and returning to the optical receiver 13 (considered here as the proportion reflected in the purge region 24 and returning to the optical receiver 13).

TABLE 1

|  | Measurement target gas passage | Purge region |
|---|---|---|
| Component concentration | A | B |
| Transmittance | C | D |

$$x = \frac{A \times C + B \times D}{C + D} \quad (2)$$

Here, the purge region 24 is only filled with the purge gas that does not include the components to be measured. Therefore, the component concentration B of the measurement target gas in the purge region 24 is 0. Accordingly, Equation (2) can be transformed into Equation (3) below.

$$x = \frac{A \times C}{C + D} \quad (3)$$

If none of the laser light 11a emitted from the optical emitter 11 is reflected in the purge region 24 to return to the optical receiver 13, the transmittance D of the laser light 11a reflected in the purge region 24 and returning to the optical receiver 13 (the proportion reflected in the purge region 24 and returning to the optical receiver 13) becomes 0. Accordingly, it follows from Equation (3) that the component concentration calculated by the laser gas analyzer 100 (concentration index x) is equal to the actual component concentration A of the measurement target gas. If, however, the relative positions of the laser light 11a and the separation wall 26 change due to vibration of the probe 20, then more of the laser light 11a is blocked by the wall portion 26w and returns to the optical receiver 13, and the transmittance D of the laser light 11a reflected in the purge region 24 and returning to the optical receiver 13 (the proportion reflected in the purge region 24 and returning to the optical receiver 13) increases. Accordingly, it follows from Equation (3) that the component concentration calculated by the laser gas analyzer 100 (concentration index x) becomes smaller than the actual component concentration A of the measurement target gas. The difference between x and A is the error in the component concentration calculated by the laser gas analyzer 100.

In one or more embodiments, the surface of the separation wall 26 facing the optical emitter 11 (blasted surface 26b) is blasted, as described above. Hence, even if the laser light 11a is blocked by the wall portion 26w, the light reflected by the blasted surface 26b is diffused, and the amount of light returning to the optical receiver 13 can effectively be reduced.

In the above example, the surface of the separation wall 26 on which laser light 11a can be irradiated is blasted, but this example is not limiting. Surface treatment other than blasting may be performed to form a minute unevenness on the surface of the separation wall 26 facing the optical emitter 11 for diffusion of reflected light. When forming the separation wall 26 by casting or the like, a minute unevenness can be formed on the separation wall 26 by forming a minute unevenness in the casting mold. The size of the minute unevenness in this case corresponds to the size of the minute unevenness obtained by the above-described blasting. Instead of providing a minute unevenness to diffuse the reflected light, surface treatment may be performed for the laser light 11a to be absorbed. For example, the surface that can be irradiated by the laser light 11a may be dyed black.

Next, the configuration of the measurement target gas passage 22 at the reflector 28 side is described with reference to FIG. 5 and FIG. 6A through FIG. 6C.

Figure 5:
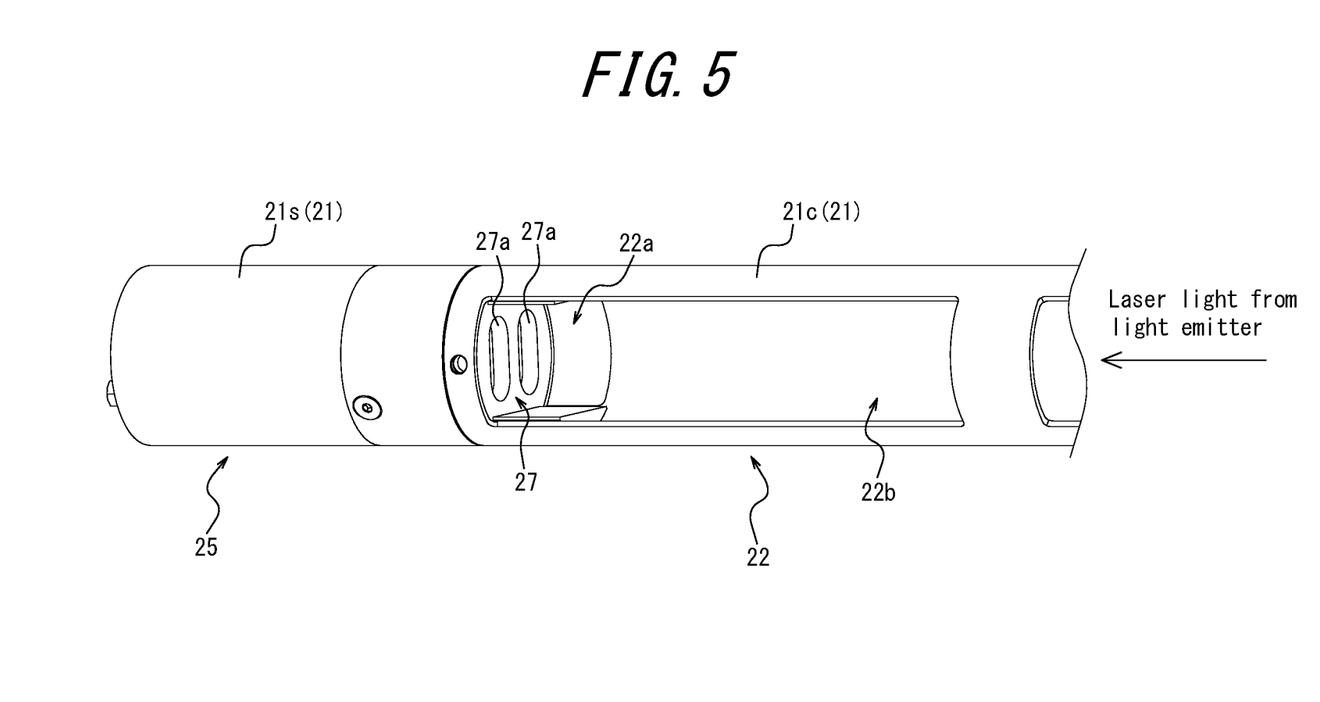
FIG. 5 is an enlarged perspective view near a separation wall on a reflector side in the laser gas analyzer according to one or more embodiments of the present invention.

FIG. 5 illustrates the configuration of the measurement target gas passage 22 at the reflector 28 side. The background is the upstream side of the measurement target gas, and the foreground is the downstream side of the measurement target gas. Accordingly, the measurement target gas flows from the background to the foreground in a substantially vertical direction on the page in FIG. 5. As illustrated, the measurement target gas passage 22 includes an upstream opening 22a and downstream openings 22b, as at the optical emitter 11 side. In one or more embodiments, the upstream opening 22a and downstream openings 22b are roughly symmetrical in the optical axis direction with respect to the measurement target gas passage 22 and have the same functions as the openings disposed on the optical emitter 11 side.

Figure 6A:
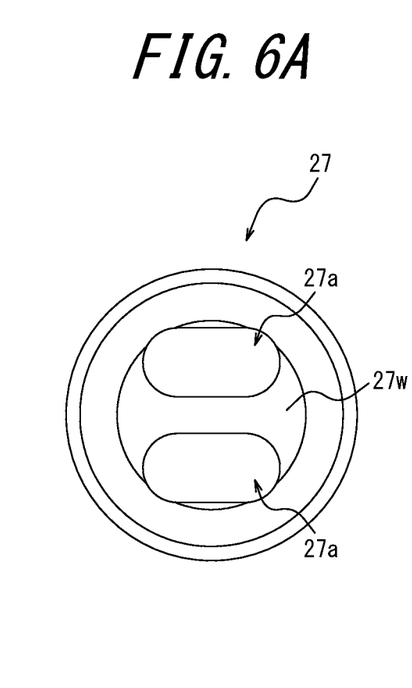
FIG. 6A illustrates the configuration of the separation wall on the reflector side.
Figures 6B, 6C:
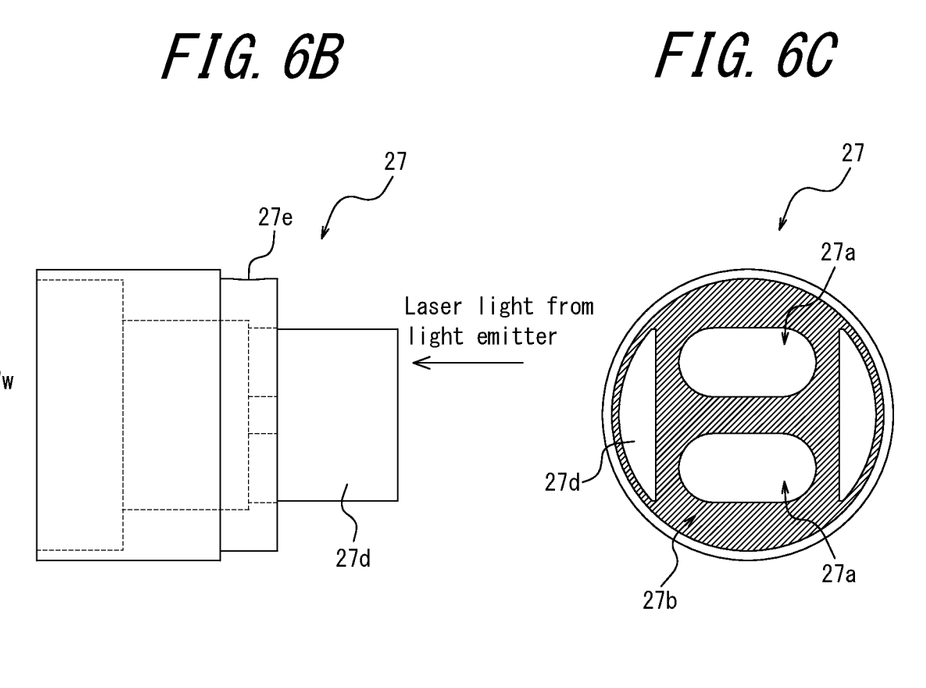
FIG. 6B illustrates the configuration of the separation wall on the reflector side.
FIG. 6C illustrates the configuration of the separation wall on the reflector side.

FIG. 6A through FIG. 6C illustrate the separation wall 27 (second separation wall) in FIG. 5, where FIG. 6A is a left view, FIG. 6B is a front view, and FIG. 6C is a right view. The separation wall 27 includes a wall portion 27w that defines the boundary between the measurement target gas passage 22 and the purge region 25 (second purge region), two holes 27a formed in the wall portion 27w, a mating portion 27e for mating and fixing the separation wall 27 to the central housing 21c, and a guide 27d for guiding the mating portion 27e into the central housing 21c when the separation wall 27 is mated and fixed to the central housing 21c. The separation wall 27 can be made of material such as SUS316. This example is not limiting, however. The separation wall 27 can be made of various other metal materials.

FIG. 6C is a right view of the separation wall 27, illustrating the separation wall 27 as seen from the direction of incidence of the laser light 11a. The hatched portion in FIG. 6C indicates a blasted surface 27b that has been blasted. Blasting the surface of the separation wall 27 facing the optical emitter 11 in this way can reduce the amount of light returning from the separation wall 27, which is not an optical component, to the optical receiver 13 so that only the laser light 11a that has traversed the intended optical path returns to the optical receiver 13.

Unlike the blasted surface 26b provided on the separation wall 26, the blasted surface 27b provided on the separation wall 27 is not an essential element. The reason is that the laser light 11a that is emitted from the optical emitter 11, is reflected at the wall portion 27w, and returns to the optical receiver 13 has passed forward and back through the measurement target gas passage 22 and has been subjected to light absorption by the measurement target gas, like the laser light 11a that traverses the intended optical path. In terms of improving the measurement accuracy of the component concentration, it is therefore considered that the presence of some laser light 11a reflected by the wall portion 27w to return to the optical receiver 13 will not greatly affect the measurement accuracy of the component concentration. The blasted surface 27b may be provided on the separation wall 27, however, so that only laser light 11a traversing the intended optical path returns to the optical receiver 13. The blasted surface 27b of the separation wall 27 may be formed by the same processing as the blasted surface 26b of the separation wall 26. Alternatively, a minute unevenness may be formed, or surface treatment may be performed, by a different method than for the blasted surface 26b.

The purge region 25 is disposed on the reflector 28 side of the measurement target gas passage 22, as illustrated in FIG. 1 and FIG. 5. The purge region 25 is a region surrounded by the side housing 21s and the separation wall 27 and filled by purge gas supplied from the non-illustrated purge gas supplier. As in the purge region 24, the supplied purge gas is discharged through the holes 27a of the separation wall 27. Members disposed on the inside, such as the reflector 28, can be protected from dust and other matter by the purge region 25 being filled with the purge gas. In one or more embodiments, the reflector 28 may be a corner cube prism, for example, that reflects laser light 11a from the optical emitter 11 at an angle of substantially 180°. Filling the purge region 25 with the purge gas can prevent the measurement target gas from flowing into the purge region 25, thereby maintaining a stable optical path length over which the laser light 11a is exposed to the measurement target gas.

In one or more embodiments, a flange 29 is formed to project radially outward from the outer circumferential surface of the housing 21. The laser gas analyzer 100 is fixed to the pipe 30, through which the measurement target gas flows, by the flange 29 being fixed to the pipe 30. The flange 29 may, for example, be attached to the pipe 30 in a manner allowing adjustment of the inclination.

As described above, the laser gas analyzer of one or more embodiments includes the optical emitter 11 that irradiates laser light 11a onto a measurement target gas, the reflector 28 that reflects the laser light 11a after the laser light 11a passes through the measurement target gas, the optical receiver 13 that receives the laser light 11a reflected by the reflector 28, the controller 15 that controls the optical emitter 11 and processes an output signal from the optical receiver 13, the tubular measurement target gas passage 22 disposed in a space between the optical emitter 11 and the reflector 28 and including the openings 22a, 22b into and out of which the measurement target gas flows, the purge region 24 (first purge region) disposed on the optical emitter 11 side of the measurement target gas passage 22 and filled with a purge gas not including the measurement target gas, and the separation wall 26 (first separation wall) defining a boundary between the measurement target gas passage 22 and the purge region 24 and including the hole 26a through which the laser light 11a can pass. The surface of the separation wall 26 facing the optical emitter 11 is a surface treated to promote diffusion or absorption of the laser light 11a. This configuration achieves an effect not attainable with PTL 1, namely the provision of a physical boundary between the measurement target gas passage 22 and the purge region 24 to stabilize the optical path length of exposure to the measurement target gas while suppressing unwanted light returning to the optical receiver 13 due to provision of the physical boundary, thereby improving the accuracy with which the component concentration of the measurement target gas is detected.

The laser gas analyzer of one or more embodiments further includes the purge region 25 (second purge region) disposed on the reflector 28 side of the measurement target gas passage 22 and filled with a purge gas, and the separation wall 27 (second separation wall) defining a boundary between the measurement target gas passage 22 and the purge region 25 and including the hole 27a through which the laser light 11a can pass. A surface of the separation wall 27 facing the optical emitter 11 has been subjected to surface treatment to promote diffusion of the laser light 11a. This configuration can provide a physical boundary between the measurement target gas passage 22 and the purge region 25 to further stabilize the optical path length of exposure to the measurement target gas and can cause only laser light 11a that has traversed the intended optical path to return to the optical receiver 13.

In one or more embodiments, blasting is adopted as the surface treatment performed on at least one of the separation walls 26, 27. This configuration allows the surface treatment required for removal of unwanted light to be performed easily and inexpensively.

In one or more embodiments, the blasted surface 26b is blasted with an abrasive having a relatively large particle size to finish the blasted surface 26b to a high surface roughness. The diffuse reflection component of light reflected by the blasted surface 26b can thereby be increased, effectively reducing the amount of light returning to the optical receiver 13.

In one or more embodiments, the position of the optical emitter 11 is adjustable relative to the separation wall 26 in direction orthogonal to the optical axis. This configuration allows the laser light 11a to be adjusted so as to pass through the center of the hole 26a provided in the separation wall 26. The laser light 11a can therefore be made less likely to be blocked by the wall portion 26w of the separation wall 26 when the probe 20 vibrates. Furthermore, the position of the optical emitter 11 can be readjusted if the laser light 11a is blocked due to the probe 20 bending under its own weight.

The embodiments of the present invention are based on the drawings and on examples, but it should be noted that a person of ordinary skill in the art could easily make a variety of modifications and adjustments on the basis of the present disclosure. Therefore, such changes and modifications are to be understood as included within the scope of the invention. For example, the functions and the like included in the various components may be reordered in any logically consistent way. Furthermore, components may be combined into one or divided. Such embodiments are also to be understood as falling within the scope of the present invention.

For example, the blasted surfaces 26b, 27b of one or more embodiments are only provided on the surface of the separation walls 26, 27 facing the optical emitter 11, but this configuration is not limiting. A surface of the separation walls 26, 27 other than the surface facing the optical emitter 11, such as the inner surface, may also be blasted.

When the position of the laser light 11a is adjusted relative to the holes 26a, 27b of the separation walls 26, 27 of one or more embodiments, all of the laser light 11a passes through the holes 26a, 27b without striking the wall portions 26w, 27w. However, this configuration is not limiting. The beam diameter of the laser light 11a may be set larger than the holes 26a, 27a so that a portion of the laser light 11a always strikes the blasted surfaces 26b, 27b.

EXAMPLES

Examples 1, 2 and a Comparative Example were produced to confirm the effects of one or more embodiments of the present invention. Examples 1, 2 include the blasted surface 26b of one or more embodiments, whereas the surfaces facing the optical emitter 11 in the Comparative Example are not blasted. Table 2 lists the specifications of each Example and the Comparative Example.

TABLE 2

| Example/Comparative Example | Separation wall specifications |
|---|---|
| Comparative Example | no blasting |
| Example 1 | blasting (blasting medium A) |
| Example 2 | blasting (blasting medium B) |

In Table 2, the blasting medium A and the blasting medium B are abrasives used for blasting and have different particle size, which is the degree of fineness of the particles. The blasting medium B is an abrasive with a larger particle size than the blasting medium A. The component to be measured in the measurement target gas is $O_2$, and the distance from the flange 29 to the tip of the probe 20 is 2 m. Since the length of the measurement target gas passage 22 along the optical axis is 50 cm, the optical path length over which the laser light 11a is exposed to the measurement target gas is 1 m.

Table 3 through Table 5 list the transmittance in the measurement target gas passage 22 and the purge region 24, the concentration index x of the laser gas analyzer 100, and the like for the Comparative Example, Example 1, and Example 2, respectively. The actual component concentration of the component to be measured ($O_2$) is 20.9.

TABLE 3

| Comparative Example (no blasting) | Measurement target gas passage | Purge region |
|---|---|---|
| Component concentration | 20.9 | 0 |
| Transmittance [%] | 1.7 | 0.36 |
| Concentration index x of laser gas analyzer 100 | 17.2 | |

TABLE 4

| Example 1 (blasting medium A) | Measurement target gas passage | Purge region |
|---|---|---|
| Component concentration | 20.9 | 0 |
| Transmittance [%] | 1.7 | 0.03 |
| Concentration index x of laser gas analyzer 100 | 20.5 | |

TABLE 5

| Example 2 (blasting medium B) | Measurement target gas passage | Purge region |
|---|---|---|
| Component concentration | 20.9 | 0 |
| Transmittance [%] | 1.7 | 0.01 |
| Concentration index x of laser gas analyzer 100 | 20.8 | |

The results in Table 3 through Table 5 demonstrate that as compared to the Comparative Example in which the separation wall 26 is not blasted, Examples 1 and 2 with the blasted surface 26b reduce the transmittance (the proportion reflected by the separation wall 26 and returning to the optical receiver 13) in the purge region 24 by a factor of 1/10 or less, so that the concentration index x of the laser gas analyzer 100 approaches the actual component concentration of 20.9. The reason why Example 2 can reduce the transmittance in the purge region 24 more than Example 1 is thought to be that forming the blasted surface 26b by blasting with an abrasive having a large particle size finishes the surface to a higher surface roughness, thereby increasing the diffuse reflection component of light reflected by the blasted surface 26b and effectively reducing the amount of light returning to the optical receiver 13.

The transmittance is a parameter indicating the (optical intensity after light absorption/optical intensity before light absorption). The laser gas analyzer 100 of one or more embodiments can be set to a certain state with 100% transmittance through internal multiplication by a coefficient. Accordingly, it should be noted that the transmittance in Table 3 through Table 5 does not refer to an absolute value, but rather to the ratio between the transmittance in the measurement target gas passage 22 and the transmittance in the purge region 24.

Although the disclosure has been described with only a limited number of embodiments, those skilled in the art, having benefit of this disclosure, will appreciate that various other embodiments may be devised without departing from the scope of the present invention. Accordingly, the scope of the invention should be limited only by the attached claims.

The invention claimed is:

1. A laser gas analyzer comprising:
   an optical emitter that irradiates laser light onto a measurement target gas;
   a reflector that reflects the laser light after the laser light passes through the measurement target gas;
   an optical receiver that receives the reflected laser light;
   a controller that controls the optical emitter and processes an output signal from the optical receiver;
   a tubular measurement target gas passage disposed between the optical emitter and the reflector and comprising an opening that allows the measurement target gas to flow into and out of the measurement target gas passage;
   a first purge region disposed on the optical emitter side of the measurement target gas passage and filled with a purge gas without a component to be measured in the measurement target gas; and
   a first separation wall that defines a boundary between the measurement target gas passage and the first purge region, and comprising a hole through which the laser light passes;
   wherein a surface of the first separation wall that faces the optical emitter is uneven to diffuse the laser light, or has been subjected to surface treatment to diffuse or absorb the laser light.

2. The laser gas analyzer of claim 1, further comprising:
   a second purge region disposed on the reflector side of the measurement target gas passage and filled with a purge gas; and
   a second separation wall that defines a boundary between the measurement target gas passage and the second purge region, and comprising a hole through which the laser light passes;
   wherein a surface of the second separation wall that faces the optical emitter is uneven to diffuse the laser light, or has been subjected to surface treatment to diffuse or absorb the laser light.

3. The laser gas analyzer of claim 1, wherein the surface treatment is blasting.

4. The gas analyzer of claim 1, wherein a position of the optical emitter is adjustable relative to the first separation wall in a direction orthogonal to an optical axis of the laser light.

* * * * *